United States Patent [19]

Clancy, III et al.

[11] Patent Number: 5,681,352

[45] Date of Patent: Oct. 28, 1997

[54] METHOD AND APPARATUS FOR ANCHORING SURGICAL TIES TO BONE

[75] Inventors: Edward William Clancy, III, Livonia, Mich.; Mark Gerard Urbanski, San Diego, Calif.

[73] Assignee: Kinetikos Medical Incorporated, San Diego, Calif.

[21] Appl. No.: 610,551

[22] Filed: Mar. 6, 1996

[51] Int. Cl.⁶ .................................................. A61B 17/04
[52] U.S. Cl. .................................................... 606/232
[58] Field of Search .............................. 606/232, 139, 606/60, 104, 72, 73, 75

[56] References Cited

U.S. PATENT DOCUMENTS

| | | | |
|---|---|---|---|
| D. 269,041 | 5/1983 | Dohogne | D24/26 |
| D. 272,764 | 2/1984 | Dohogne | D24/33 |
| D. 283,083 | 3/1986 | Stednitz | D3/74 |
| D. 320,452 | 10/1991 | Carchidi | D24/172 |
| D. 321,055 | 10/1991 | Carchidi | D24/152 |
| D. 323,070 | 1/1992 | Anderson et al. | D6/317 |
| D. 323,214 | 1/1992 | Carchidi | D24/143 |
| D. 354,352 | 1/1995 | Selman | D24/133 |
| 3,910,281 | 10/1975 | Kletschka et al. | 128/335 |
| 4,244,360 | 1/1981 | Dohogne | 128/92 |
| 4,308,863 | 1/1982 | Fischer | 128/92 |
| 4,393,868 | 7/1983 | Teague | 128/92 |
| 4,414,966 | 11/1983 | Stednitz | 128/92 |
| 4,450,834 | 5/1984 | Fischer | 128/92 |
| 4,454,870 | 6/1984 | Schwentker | 128/75 |
| 4,522,200 | 6/1985 | Stednitz | 128/92 |
| 4,667,660 | 5/1987 | Eingorn | 128/75 |
| 4,760,844 | 8/1988 | Kyle | 128/92 |
| 4,923,458 | 5/1990 | Fischer | 606/59 |
| 4,936,843 | 6/1990 | Sohngen | 606/54 |
| 4,955,947 | 9/1990 | Hajianpour | 128/748 |
| 5,002,550 | 3/1991 | Li | 606/139 |
| 5,010,902 | 4/1991 | Rambo et al. | 128/888 |
| 5,041,129 | 8/1991 | Hayhurst et al. | 606/232 |
| 5,047,034 | 9/1991 | Sohngen | 606/87 |
| 5,203,787 | 4/1993 | Noblitt et al. | 606/232 |
| 5,300,071 | 4/1994 | Browner et al. | 606/57 |
| 5,306,278 | 4/1994 | Dahl et al. | 606/96 |
| 5,334,204 | 8/1994 | Clewett et al. | 606/73 |
| 5,336,224 | 8/1994 | Selman | 606/69 |
| 5,356,413 | 10/1994 | Martin et al. | 606/75 |
| 5,522,846 | 6/1996 | Bonutti | 606/232 |
| 5,534,012 | 7/1996 | Bonutti | 606/232 |

*Primary Examiner*—Michael Buiz
*Assistant Examiner*—Tina T. D. Pham
*Attorney, Agent, or Firm*—Baker, Maxham, Jester & Meador

[57] ABSTRACT

An elongated anchor and an attached surgical tie are secured to a bone region for use in suturing ligaments, tendons, and the like to the bone. First, an entry hole of predetermined size is drilled in the bone, extending through the cortical layer into the cancellous layer. The hollow shaft of a disposable installation tool is inserted into the entry hole. The shaft has a distal end attached to an apertured deflecting nose, which preferably includes an rounded formation of resilient fingers. The tool houses an elongated anchor with a pair of sides closely interconnected by a bridge, where the sides together define an anchor body having a relatively small cross-section and a pair of opposing ends. The tool also houses a continuous tie that passes around the bridge. A plunger is slidably advanced down the tool's hollow shaft, advancing the anchor lengthwise through the tool shaft and nose into the cancellous layer of bone. Tightening the tie pulls a rounded end of the anchor against the deflecting nose; by tightening the tie even more, the anchor is rotated against the rounded deflecting nose until the anchor body is at angle to the entry hole. Further tightening of the tie pulls the anchor body firmly against the cortical layer, such that the anchor body spans the entry hole and locks the anchor in place.

19 Claims, 13 Drawing Sheets

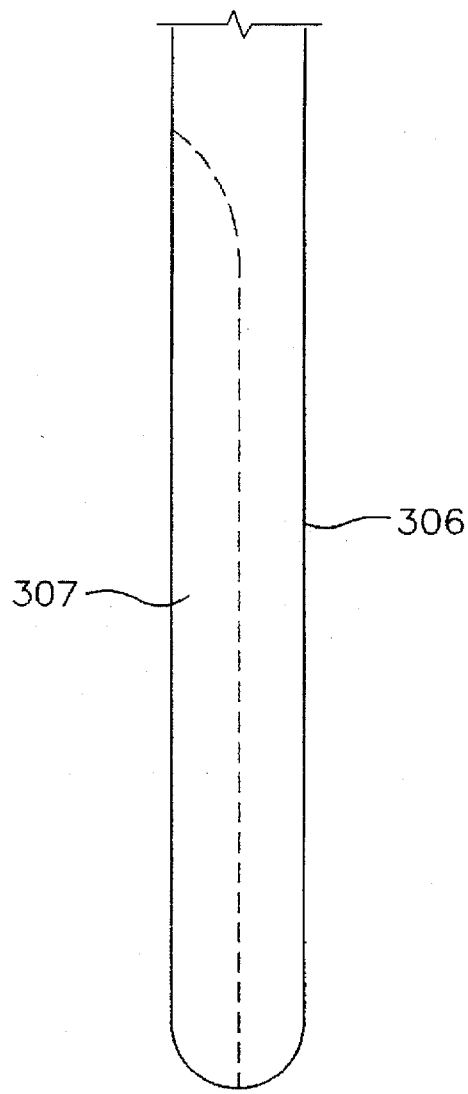 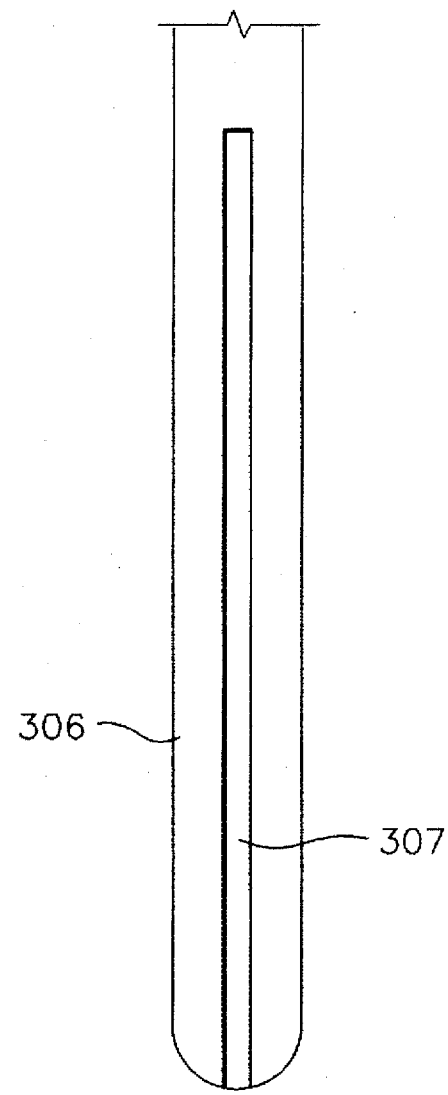
FIG. 3A  FIG. 3B
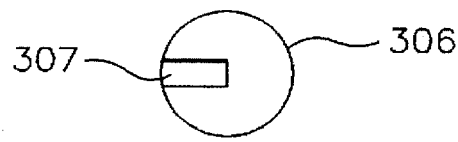
FIG. 3C

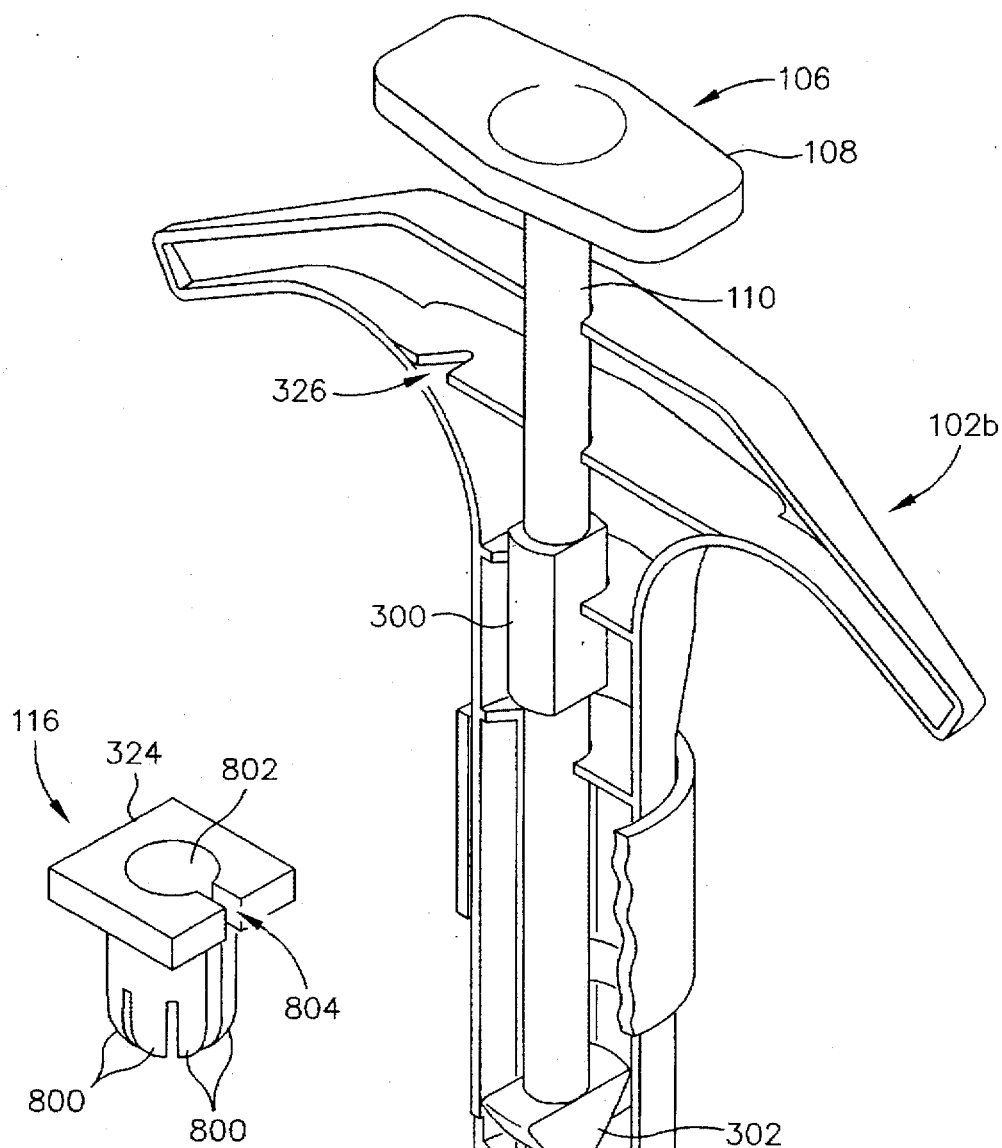
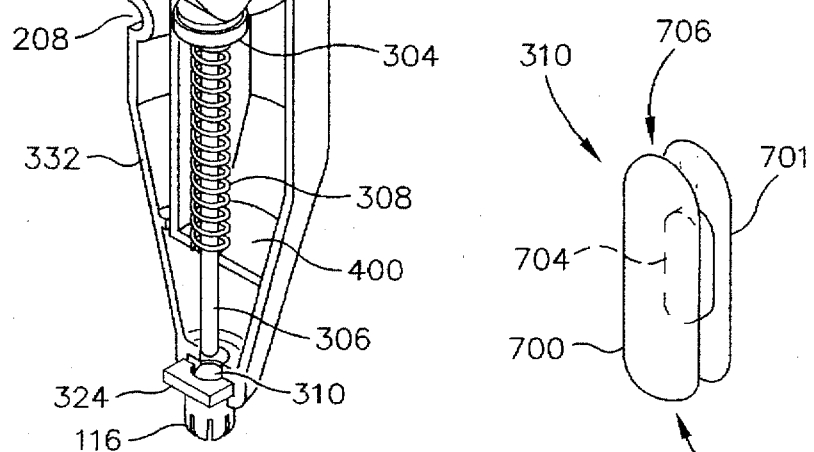
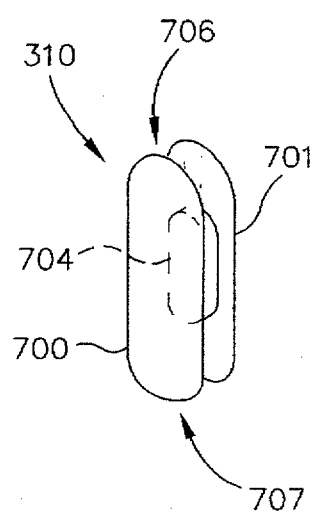
FIG. 8
FIG. 4
FIG. 7

METHOD AND APPARATUS FOR ANCHORING SURGICAL TIES TO BONE

BACKGROUND OF THE INVENTION

1. Field of the Invention

This invention relates to the anchoring of surgical ties to bone. More, particularly, the invention concerns a method and apparatus for securing an elongated anchor against the cortical bone within the cancellous region of bone.

2. Description of Related Art

In the medical arts, many different reasons exist for attaching objects to bone. Certain prosthetic devices, for example, can be rigidly integrated to bones to provide artificial joints. In other applications, pins can be attached to a bone to firmly support the bone during healing. Lending permanent support to weak areas of bone is still another reason for attaching objects to bones.

One of the most important reasons for attaching objects to bone, however, is to repair tendons and ligaments. Depending upon the nature and location of a musculoskeletal injury, the injury may incapacitate a muscle, joint, or even an entire limb. Therefore, it is crucial to have a reliable means for attaching the tendon or ligament to the bone.

Over the years, a number of different devices have been developed for this purpose. Some of the more simple solutions have employed screws, staples, cement, and sutures. For some applications, these simple devices may not be completely adequate, as discussed in the background description in U.S. Pat. No. 4,898,156.

Some more advanced approaches are shown in U.S. Pat. Nos. 4,898,156, 4,899,743, and 4,946,468. These systems involve various bone anchor devices and installation tools. U.S. Pat. No. 4,898,156, for example, describes a suture anchor that includes a coupling member, a resilient elastic barb, and a structure that attaches an end of a suture to the anchor.

U.S. Pat. No. 5,203,787 discloses an arrangement for attaching a suture to a bone, where the suture is attached to a central portion of a device at a point offset from the device's longitudinal axis. The device may be formed by a steel rod bent into a 360° loop, for example. The device and an attached suture are placed into the cancellous region of bone through a hole formed in the bone. The device's ends are preferably formed with sharp points, such that the device rotates when pulled outward by its suture, causing the device's ends to engage the bone and prevent removal of the device and suture from the hole.

Many users may be completely satisfied with the various bone attachment schemes discussed above. Nonetheless, the rapid pace of competition and advancement in the surgical arts drives engineers and doctors to continually improve surgical tools and procedures. Therefore, doctors and patients alike would certainly benefit by having a bone attachment system with increased convenience, reliability, and effectiveness.

SUMMARY OF THE INVENTION

The present invention concerns a system for securing an elongated anchor and an attached surgical tie to a bone region by installing the anchor within a cancellous region of the bone. The invention also concerns a method for installing a bone anchor. In this method, an entry hole of predetermined size is drilled in the bone, extending through the cortical layer into the cancellous layer. A hollow tool is inserted into the entry hole. The tool has a distal end attached to a deflecting nose with a passage defined therethrough. The tool houses an elongated anchor with a pair of sides closely interconnected by a bridge, where the sides together define an anchor body having a relatively small lateral cross-section and a pair of opposing ends. The tool also houses a continuous tie that passes around the bridge.

The anchor is advanced lengthwise through the tool and out the nose into the cancellous layer of bone. The tie is then tightened sufficiently to pull an end of the anchor against the deflecting nose. By tightening the tie even more, the anchor is rotated against the deflecting nose until the anchor body is at an angle with respect to the entry hole. The tool is withdrawn from the entry hole. By further tightening the tie, the anchor body is pulled firmly against the cortical layer while spanning the entry hole, thereby locking the anchor in place.

The apparatus of the invention includes an installation tool for anchoring a surgical tie to bone. The tool, which is largely hollow, includes a distal end attached to a deflecting nose. The deflecting nose has a passage defined therethrough. An elongated anchor is housed within the passage of the nose. The anchor includes a pair of sides closely interconnected by a bridge, where the sides together define an anchor body having a relatively small lateral cross-section and a pair of opposing ends. A continuous tie, which passes around the bridge, is housed within the tool.

The tool also houses a plunger, which is slidably movable through the tool to advance the anchor through the tool and out through the deflecting nose. The deflecting nose and anchor ends are shaped such that when an anchor end is urged against the nose, the nose rotates the anchor by deflecting the anchor end.

This invention provides a number of distinct benefits. Chiefly, the invention provides doctors and patients alike with increased convenience, reliability, and effectiveness in a bone anchoring system. The invention is convenient, for instance, because the installation tool is made from inexpensive materials that can be discarded after the anchoring operation, without time-consuming cleaning, sharpening, sterilization, reloading, and other preparation. The invention is also convenient because the installation tool automatically presents needles for the surgeon to more easily grasp. The invention is reliable and effective due to a number of features, such as its simplicity of construction and operation. Additionally, the anchor is shaped to broadly and evenly distribute suture attachment forces along the cortical bone, avoiding possible damage to the cortical bone.

The details of the preferred embodiment of the present invention are set forth in the accompanying drawings and the description below. Once the details of the invention are known, numerous additional innovations and changes will become obvious to one skilled in the art having the benefit of this disclosure.

BRIEF DESCRIPTION OF THE DRAWINGS

FIG. 3A is a first side plan view of a plunger extension of the invention, illustrating a curved slot in accordance with the invention;

FIG. 3B is a second side plan view, taken 90° from the first side plan view, of the plunger extension and curved slot of the invention;

FIG. 3C is a bottom plan view of the plunger extension and curved slot of the invention;

FIG. 4 is an assembled perspective view of the installation tool of the invention;

FIG. 7 is a perspective view of an anchor embodying one aspect of the present invention;

FIG. 8 is a perspective view of a nose piece embodying one aspect of the present invention;

Like reference numbers and designations in the various drawings refer to like elements.

DETAILED DESCRIPTION OF THE INVENTION

The present invention generally concerns a system for securing a surgical tie to a bone via an elongated anchor affixed within the cancellous region of the bone. The invention contemplates a number of different features, including both method and apparatus aspects.

STRUCTURE

Figure 1:
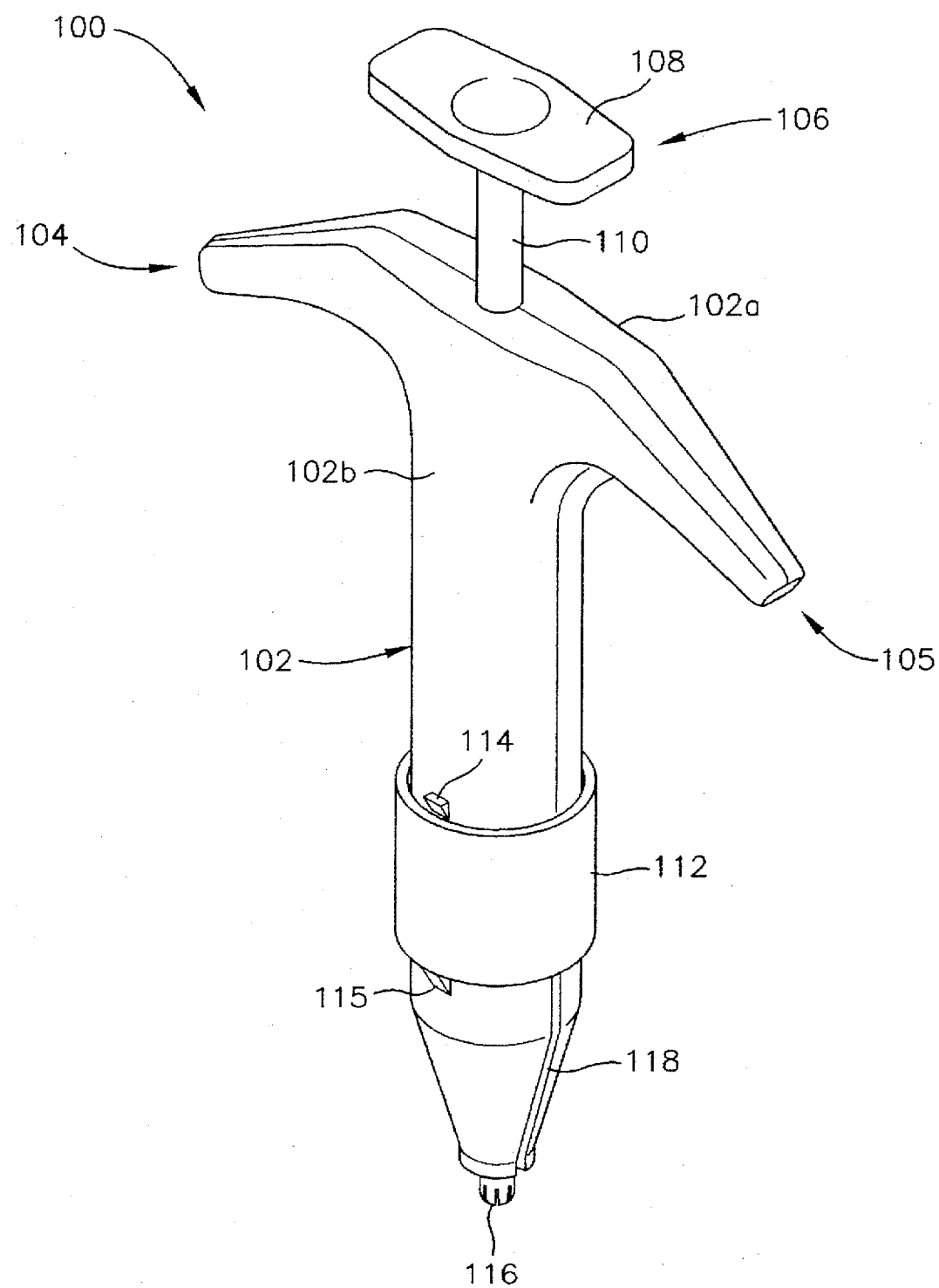
FIG. 1 is a perspective view of an installation tool embodying one aspect of the present invention.
Figure 2:
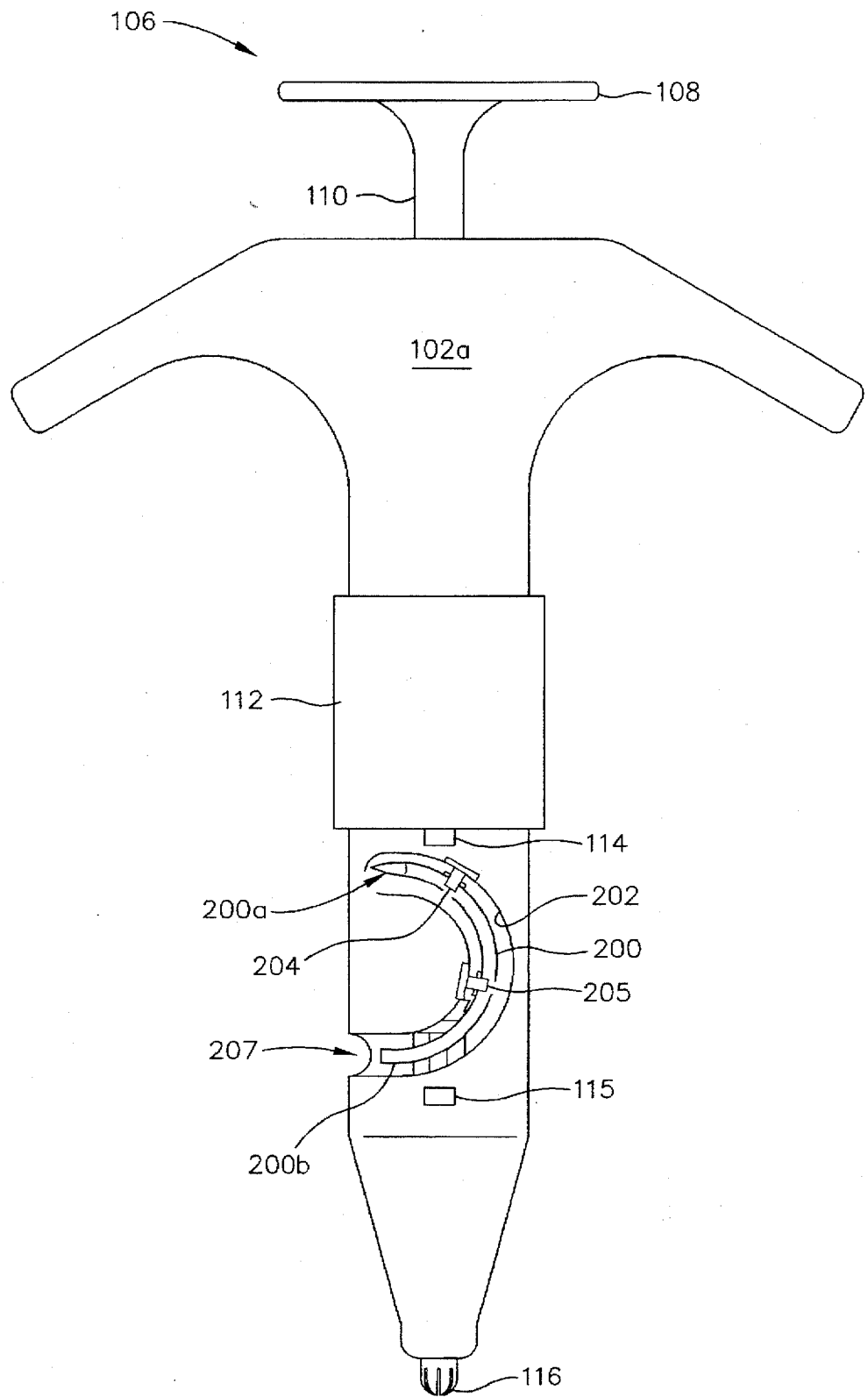
FIG. 2 is a side plan view of the installation tool of the invention, with needles exposed.

The hardware components and interconnections of the invention are exemplified by the installation tool 100 illustrated in FIGS. 1–2. The tool 100 generally includes a two-piece housing 102 having first and second parts 102a–102b that are three-dimensional mirror images of each other. The parts 102a–102b cooperatively form opposing finger grips 104–105.

A plunger 106 partially resides within the housing 102, the plunger 106 having a broad thumb-piece 108 and a central shaft 110. In FIG. 1, the central shaft 110 is only partially shown, the remaining portion residing inside the housing 102.

Figure 3:
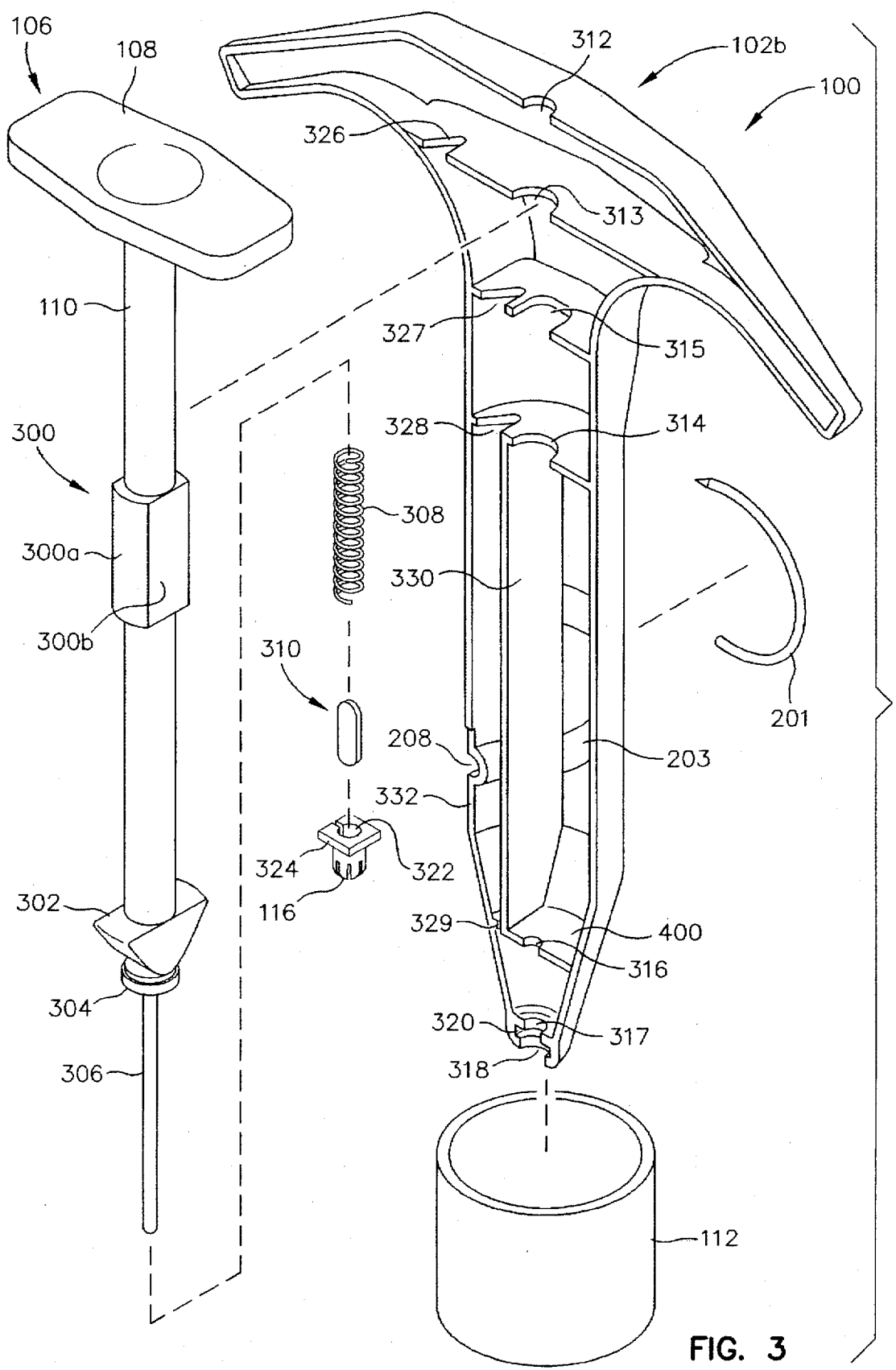
FIG. 3 is an exploded perspective view of the installation tool of the invention.

The tool 100 also preferably includes a retaining ring 112, which initially surrounds the housing 102 prior to use of the tool 100. As shown in FIG. 1, the ring 112 preferably conceals a first needle 200 (FIG. 2) and an opposing second needle 201 (FIG. 3). The needles 200, 201 preferably reside inside opposing channels 202, 203 defined in sides of the housing 102. In particular, in the preferred embodiment of the present invention, the needle 200 resides in a channel 202 defined in the housing part 102a, and the needle 201 resides in a channel 203 defined in the housing part 102b. Each of the needles has a sharp end and a blunt end, such as the sharp end 200a and blunt 200b end of the needle 200 shown in FIG. 2. Each needle is held in its respective channel by protrusions, such as the protrusions 204–205 in the case of the needle 200.

The needles 200, 201 are attached to a surgical tie, such as a suture (FIG. 5) that is used to secure a ligament, tendon, or muscle to a bone as described in greater detail below. Preferably, each needle's blunt end is hollow for receiving one end of the tie, which is subsequently secured to the needle by crimping. The retaining ring is held in place by upper and lower ramps 114, 115. The upper ramp 114 presents an inclined surface to the ring 112 enabling the ring to slide upward past the ramp 114, exposing the needles for use as shown in FIG. 2.

The tool 100 also includes a deflecting nose 116, which is held in place between the housing parts 102a–102b. As explained below, the nose 116 plays an important role in the installation of a bone anchor by the tool 100.

Plunger

To further describe the components of the tool 100, including the plunger 106 and its related parts, reference is additionally made to FIGS. 3–4. In addition to the components shown in FIGS. 1–2, the plunger 106 includes a multi-sided torsion block 300. In the illustrated example, the block 300 includes four sides: first and second sides 300a–300b, and a pair of opposing sides (not shown). The sides may have a number of different shapes, such as gently rounded shapes, or substantially flat shapes that cooperatively form a generally rectangular cross-section.

The plunger 110 also includes a needle biasing wedge 302. In the illustrated example, the wedge 302 has a generally triangular shape, the function of which is described more fully below. Beneath the wedge 302 there is a plunger stop 304, which may have a generally circular shape. Beneath the stop 304 there lies a plunger extension 306, comprising an elongated protrusion of reduced cross-sectional size in comparison to the shaft 110.

A curved slot 307 is linearly defined along the extension 306, as shown in FIGS. 3A–3C. The slot 307 is sized to receive two lengths of the surgical tie, passing along the longitudinal axis (not shown) of the extension 306, as illustrated in greater detail below.

Assembly of the Tool

To assemble the tool 100, a spring 308 is placed around the extension 306 and slid upward against the stop 304. The plunger 106 is placed against the housing part 102b, such that the shaft 110 rests in the plunger cutouts 312–314, the block 300 rests in the plunger cutout 315, and the extension 306 rests in the plunger cutouts 316–318. The cutouts 312–314 are generally rounded. The cutout 315 is enlarged to accommodate the torsion block 300 for reasons discussed below.

Also in the assembly of the tool 100, an elongated anchor 310 (FIG. 3) is deposited into an inner chamber 322 of the nose 116. The nose 116 and anchor 310 together are placed into a slot 320 of the housing part 102b. More specifically, the nose 116 includes a flange 324 sized to fit inside the slot 320.

Figure 5:
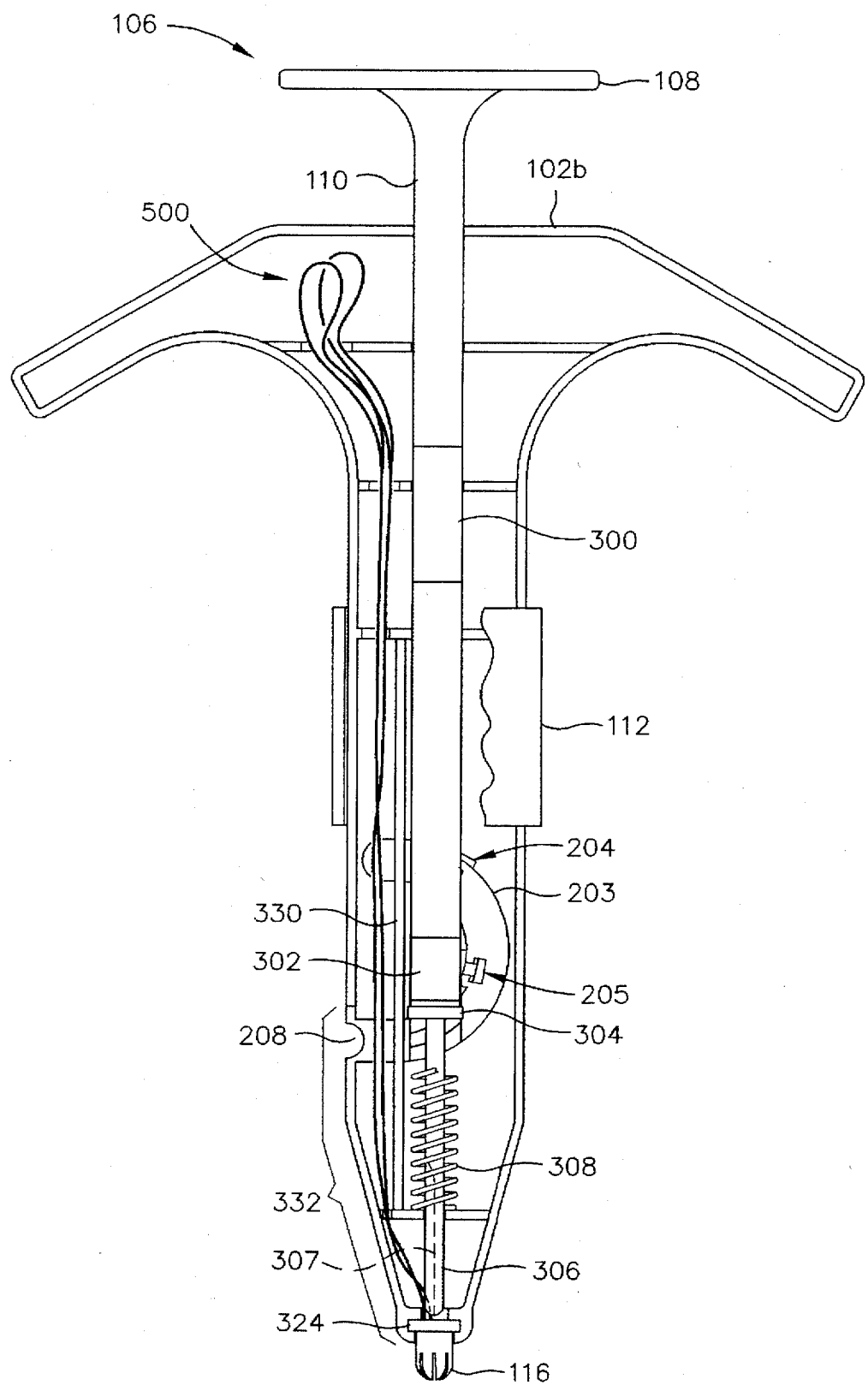
FIG. 5 is a cutaway side plan view of the installation tool of the invention.
Figure 6:
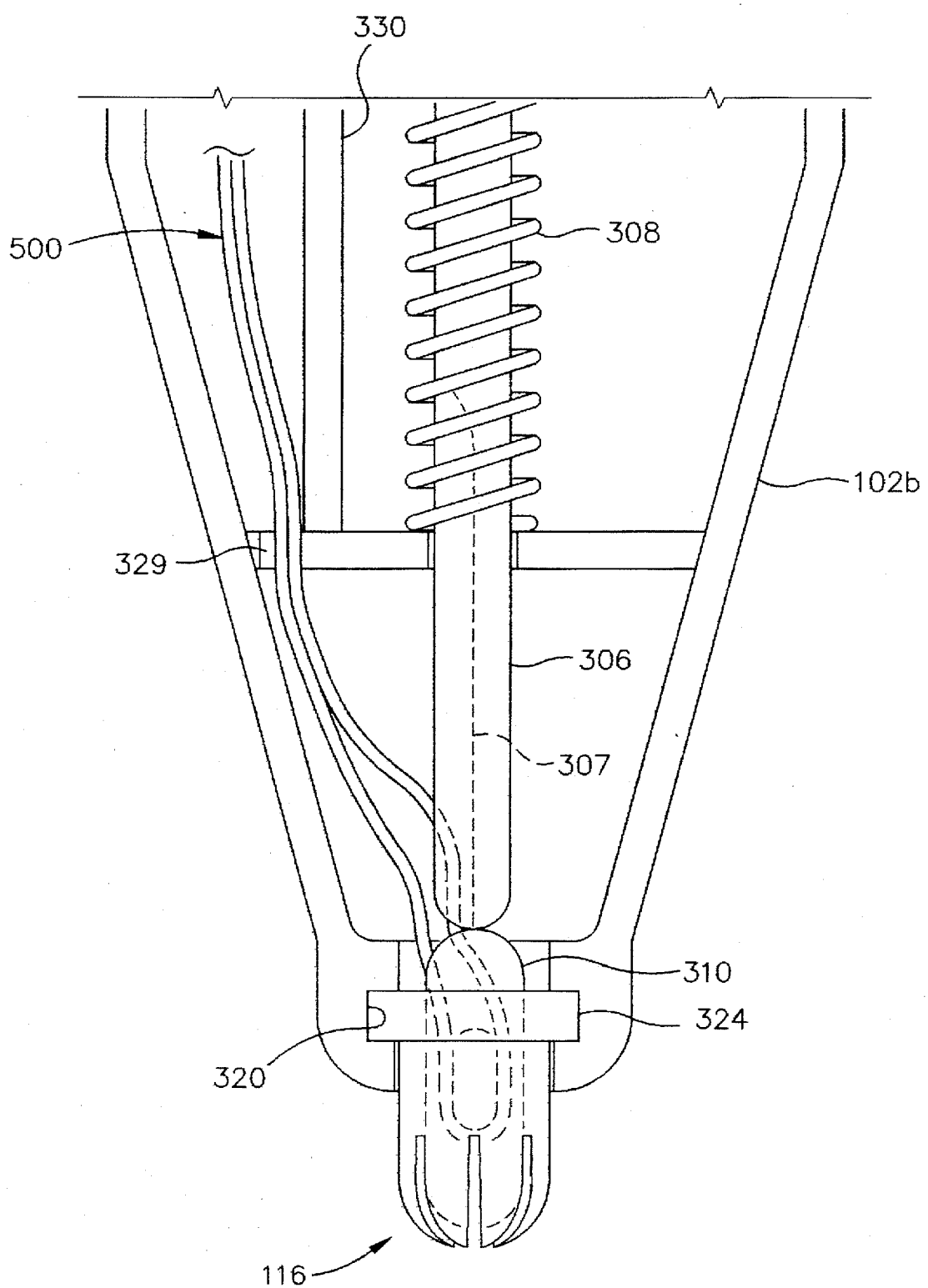
FIG. 6 is an enlarged cutaway side plan view of the installation tool of the invention.

As best shown in FIGS. 4–6, when the tool 100 is assembled the spring 308 is sandwiched between a flange 400 and the stop 304. In this position, the spring 308 urges the plunger 106 upward until the upper edges of the torsion block 300 contact the edge of the cutout 313, due to the cutout 313 being differently shaped or smaller than the block 300.

Surgical Tie and Associated Passageways

Although not shown in FIGS. 3–4 for ease of illustration, a surgical tie 500 (FIGS. 5–6) is also contained inside the housing 102. In the preferred embodiment, the tie 500 comprises a length of surgical thread having a size and tensile strength appropriate to the operation being performed. The housing parts 102a–102b define cutouts, such as the cutouts 326–329 defined in the part 102b. Each housing part 102a–102b has defined therein an inset region, such as the inset region 332 of the housing part 102b (FIGS. 3–4). When the parts 102a–102b are mated, opposing inset regions 332 form a slot 118 as shown in FIG. 1. As described in greater detail below, the slot 118 aids in removal of the tie 500 from the housing 102 after implanting the anchor 310 in a patient's bone. For this purpose, the channels 202–203 may extend around the housing 102 toward the slot 118, as shown by the complementary channel extensions 207–208 (FIGS. 2–5).

The tie passes from the needle 201 through the curved channel extension 208 into the housing 102, downward through the cutout 329 inside the housing, into the slot 307 of the extension 306, around the anchor 310, and continues to the other needle 200 along a similar path. Excess length of the tie 500 is preferably wound neatly back and forth within the housing 100, along the cutouts 326–329 of the housing 102b and the corresponding cutouts (not shown) in the housing part 102a. Wound lengths of the tie 500 are separated from the plunger assembly by a partition 330, most clearly shown in FIGS. 3 and 5–6.

Anchor

FIG. 7 illustrates the anchor 310 in greater detail. The anchor 310 includes a pair of sides 700–701 closely interconnected by a bridge 704. The sides 700–701 cooperatively form an anchor body having a pair of opposing ends 706–707. The anchor is preferably manufactured from a sturdy yet gradually bio-absorbable material. Alternatively, the anchor may be made from more permanent material, such as titanium or stainless steel.

Advantageously, the anchor body defines either flat or gently rounded surfaces, avoiding any points or edges. After the anchor 310 has been installed in a patient's bone, these features ensure that tension on the anchor is evenly distributed along the inner surface of the patient's cortical bone, as discussed below. Tension on the anchor 310 may be further distributed by providing an anchor body with a large size relative to the force of tension applied to the anchor 310. Additionally, since the anchor 310 has a small lateral cross-section, it can be inserted through a minimally intrusive hole in the patient's bone.

Nose

FIG. 8 depicts a preferred embodiment of the nose 116 in greater detail. The nose 116 has multiple curved resilient fingers 800 integrally formed on the flange 324. The flange 324 has defined therein a central aperture 802, which extends downward into a central chamber (not shown) between the resilient fingers 800. The chamber is sized to slidably accommodate the anchor 310, the chamber's cross-sectional area being slightly larger than the lateral cross-section of the anchor 310.

The flange also has a slot 804, which provides a passage between the aperture 802 and the exterior of the nose 116. As explained more fully below, the slot 804 provides a place for the tie 500 to exit the nose 116. The nose 116 may be manufactured by heat or vacuum molding, for example. The nose is preferably made from an elastic material such as polypropylene, polyethylene, a different polymer, or another suitable material.

OPERATION

FIGS. 9–15 depict a sequence of steps to illustrate an exemplary embodiment of the method aspect of the invention. Generally, the tool 100 is used to insert the anchor 310 into a region of bone, to rigidly position the anchor 310 in the bone, and to present the tie 500 and attached needles for use by a physician to connect muscle, ligament, or tendon to the bone via the anchor 310. After presentation, the physician may remove the tool 100 and dispose of it.

Configuration of Tool

Prior to using the tool 100, the tool is configured as follows. As shown in FIG. 1, the housing parts 102a–102b are connected to each other, with the ring 112 surrounding the housing 102 and residing between the ramps 114–115. The housing parts 102a–102b may be fastened by glue, heat welding, fastening device, or another suitable means.

Inside the housing 102, as shown in FIG. 5, the plunger shaft 110 is neatly housed between opposing cutouts 312–318 of the housing parts 102a–102b. The spring 308 urges the plunger 106 upward, by pressing outward against the flange 400 and the stop 304. The plunger's upward travel is limited, however, due to the contact between the torsion block 300 and the cutout 313. The extension 306 of the plunger resides against one of the rounded ends of the anchor 310. The other rounded end of the anchor 310 is supported by the resilient fingers 800 (FIG. 8) within the central aperture 802 of the nose 116.

Referring to FIGS. 2–5, the opposing needles 200–201 are firmly held in their respective channels by protrusions 204–205 therein. Each needle 200–201 is attached to an end of the tie 500, which is neatly wound back and forth in the cutouts 326–328. The partition 330 prevents the tie 500 from interfering with the operation of plunger 106, due to entanglement with the spring 308 and the like. The tie 500 extends through a cutout 329 into the slot 307 of the extension 306 and then loops around the bridge 704 (FIG. 7) of the anchor 310.

Preparation

With the tool 100 configured as described above, little preparation of the tool 100 is required prior to use by a physician or other medical personnel. Namely, the tool 100 is removed from a sterilized package (not shown), and then the ring 112 is slid upward over the ramp 114 to expose the needles.

Unlike the tool 100, preparation of the patient (not shown) is somewhat more involved. First, an incision is made to expose the region of bone where the anchor is to be installed. Then, referring to FIG. 9, a hole 900 is drilled through the hard cortical 902 region of bone. The hole 900 extends sufficiently into the relatively soft cancellous layer 904 sufficiently to receive the anchor 310, as explained below. The hole 900 has a diameter just slightly larger than the nose 116.

Insertion

Figure 9:
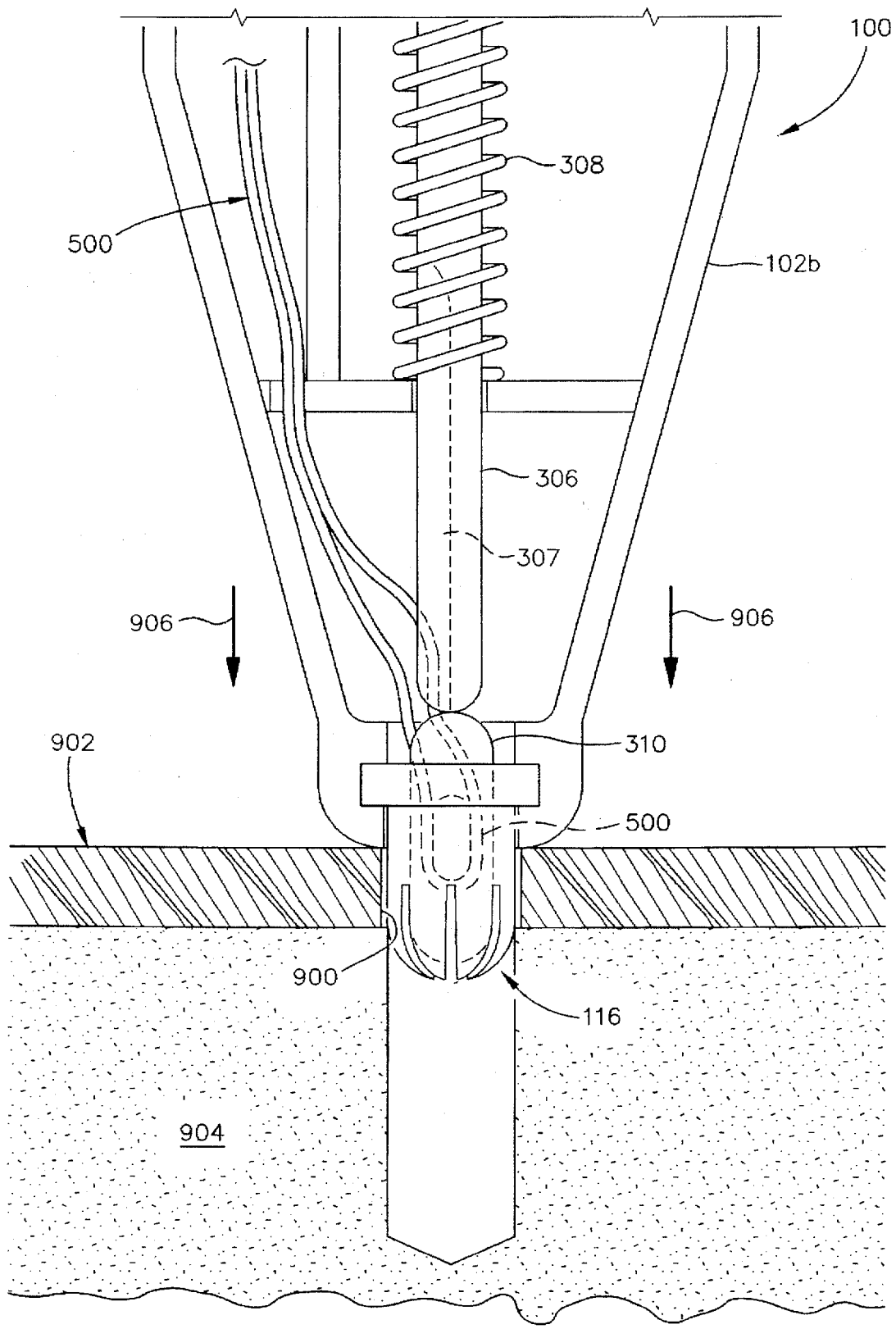
FIGS. 9–10 are enlarged cutaway side plan views of the installation tool of the invention, illustrating an installation sequence in accordance with the invention.

Having drilled the hole 900, the tool 100 is aligned with the hole 900. Then, the tool 100 is moved in a direction 906 (toward the bone) until the nose 116 is inserted into the hole 900 as shown in FIG. 9. In this position, the nose 116 protrudes slightly past the cortical 902 into the cancellous region 904 of bone.

Presentation

Figure 10:
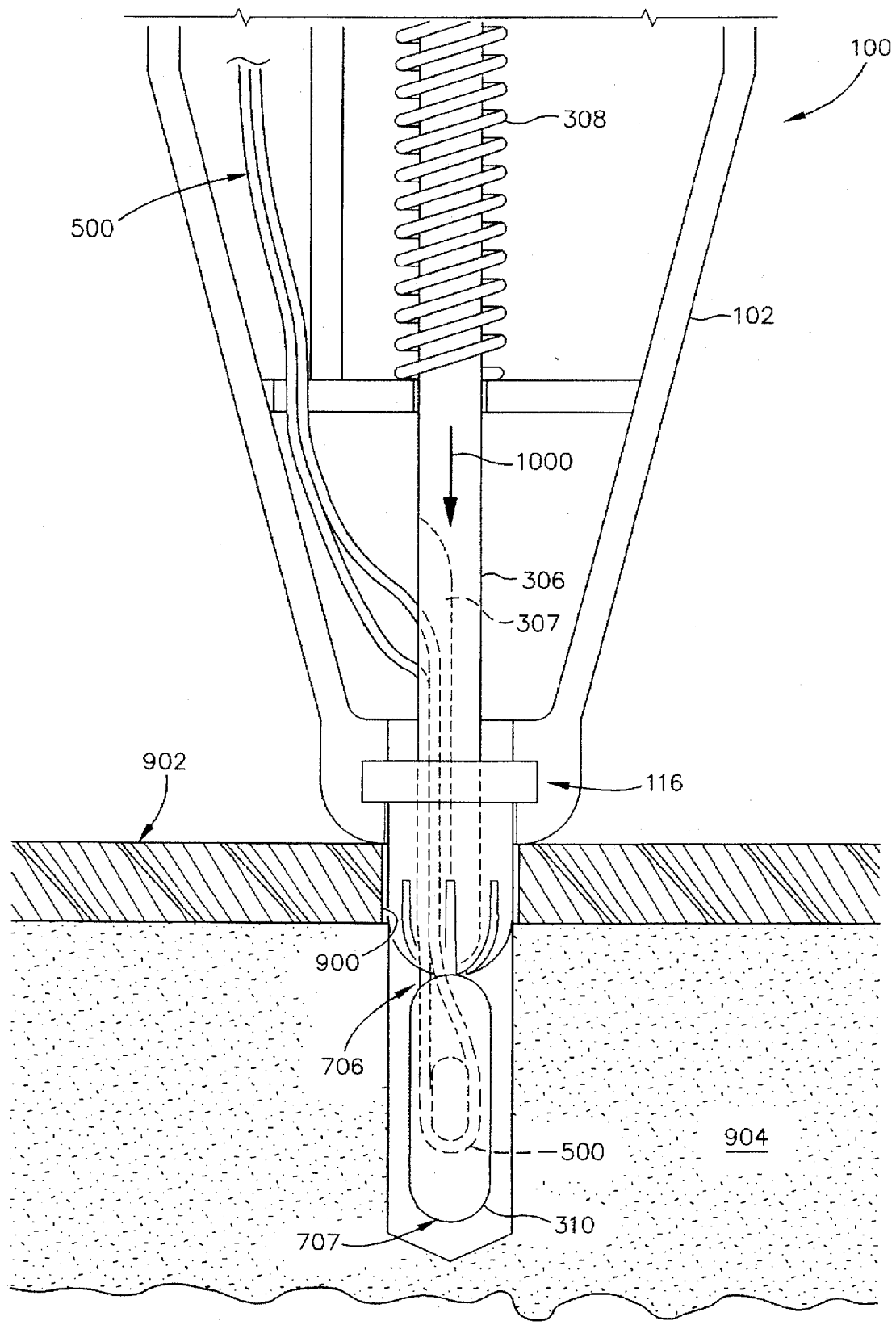

Next, the operator presses the thumb-piece 108 (FIG. 1) while retaining the finger grips 104–105 with forefinger and middle finger. As shown in FIG. 10, this moves the plunger, including the plunger extension 306, in the direction 1000 toward the bone. The extension 306 presses against the anchor 310, urging the anchor 310 into the hole 900 from its resting place inside the nose 116. The resilient fingers 800 part about the anchor 310, permitting the anchor 310 to exit the nose 116. As the plunger extension 306 moves the anchor 310 deeper into the hole 900, the anchor 310 pulls additional lengths of tie 500 from within the housing 102. The operation releases pressure on the plunger 106 when the anchor 310 exits the nose 116, as shown in FIG. 10. In this position, a rounded end of the anchor 310 abuts the rounded surface provided by the fingers 800 of the nose 116.

Figures 11, 12:
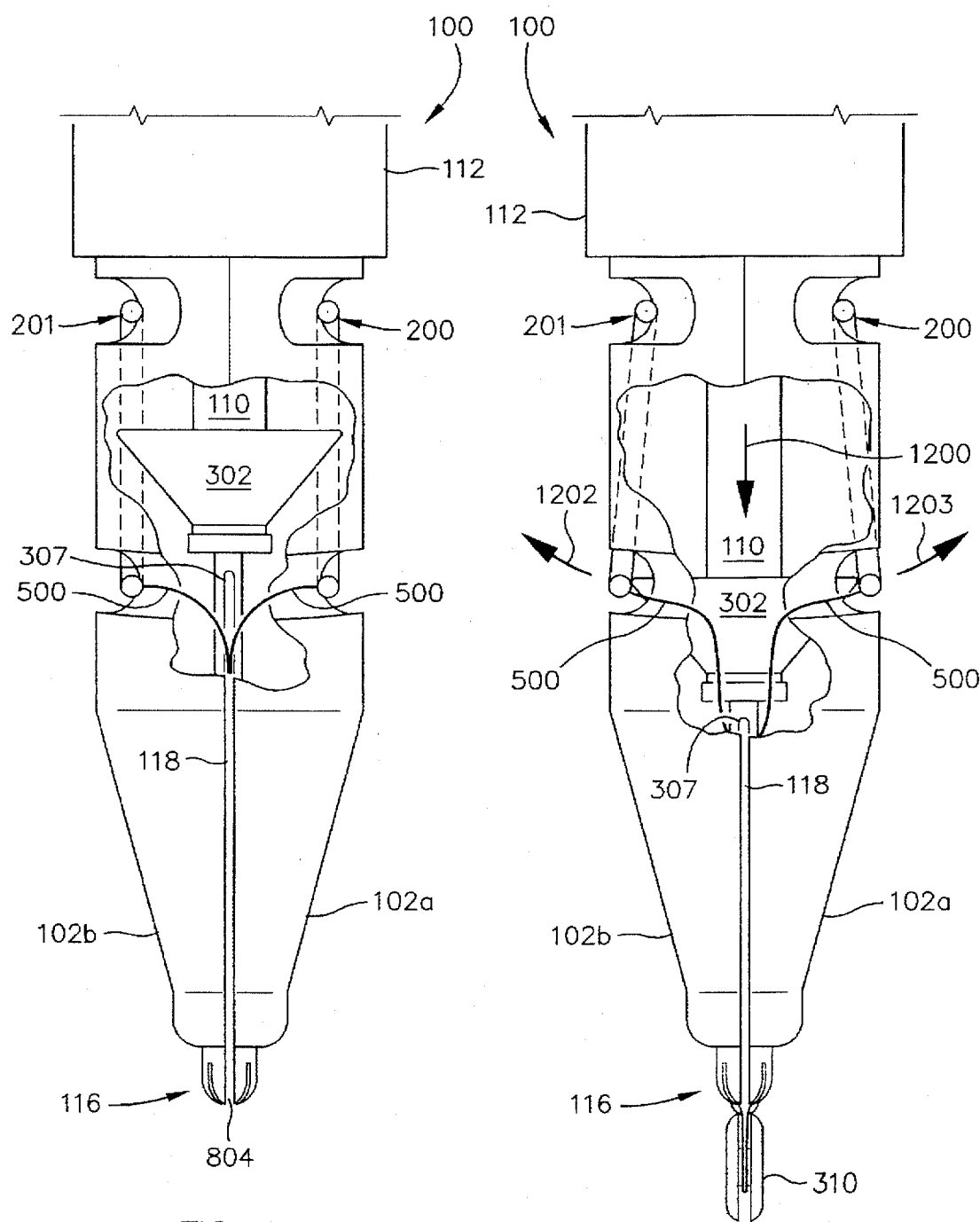
FIGS. 11–12 are partially cutaway side plan views of the installation tool of the invention, illustrating a needle presentation feature of the invention.

When pressure on the thumb-piece 108 drives the plunger shaft 110 sufficiently into the housing 102, the biasing wedge 302 simultaneously positions the needles 200–201 for use by the physician. To illustrate this process in greater detail, reference is made to FIGS. 11–12. In FIG. 11, the needles 200–201 are in a stowed position. However, as shown in FIG. 12, continued movement of the shaft 110 in the direction 1200 ultimately brings the biasing wedge 302 in contact with the lower ends of the needles 200–201. The lower surfaces of the biasing wedge 302, which are shaped to form inclined planes, urge the lower ends of the needles 200–201 outward from their respective channels 202–203 in opposing directions 1203–1202. As discussed above, the needles' lower ends are preferably their blunt ends. Thus, the biasing wedge 302 conveniently presents the needles for the physician to safely grasp.

Positioning

Figure 13:
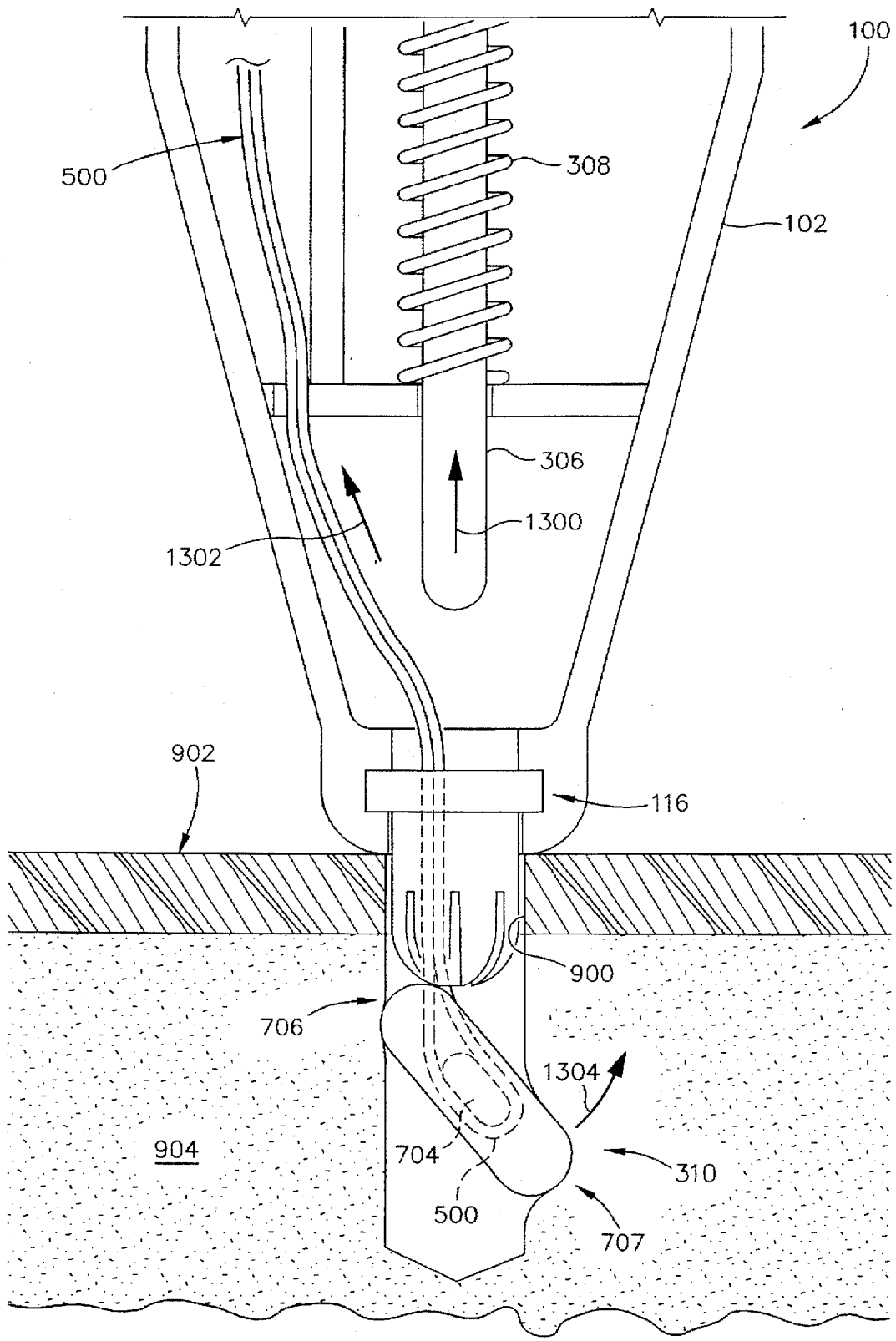
FIGS. 13–15 are enlarged cutaway side plan views of the installation tool of the invention, illustrating further steps in the installation sequence of the invention.

As shown in FIG. 13, the plunger 106 is then withdrawn in the direction 1300 to retract the extension 306 from contact with the anchor 310. After withdrawing the plunger 106, the physician grasps and pulls the needles 200–201 to completely free them from their respective storage channels. The physician must overcome the retaining force provided by the upper channel protrusions 204–205, which still hold the needles' upper ends in place.

Next, the physician pulls the needles 200–201 outward from the housing 102 sufficiently to remove the tie 500 from its resting place therein. When the entire length of tie 500 is removed from the housing 102, the physician withdraws the tie 500 in the direction 1302. This may be achieved by grasping the needles 200–201 or directly tugging on the tie 500. Pulling on the tie 500 in this fashion has the effect of pulling the anchor 310 up against the nose 116. In particular, pulling the tie 500 with a gentle, but firm force, pulls the bridge 704 toward the tool 100, ultimately urging the rounded end 706 of the anchor 310 against the rounded fingers 800. Of course, if the anchor 310 is initially deposited into the nose 116 with a reverse orientation, the rounded end 707 will be biased against the nose 116 instead.

Continued pulling on the tie 500 causes the anchor 310 to rotate as its rounded surface 706 slides against the fingers 800 of the nose 116. This rotation is caused by the large moment arm existing between the bridge 704 and the rounded end 706 and the relatively small width of the rounded end 706. Although this rotation may occur in any number of directions, FIG. 13 depicts rotation in a counter-clockwise direction 1304. This rotation of the anchor 310 effectively burrows into the cancellous layer 904, widening the hole 900.

Figure 14:
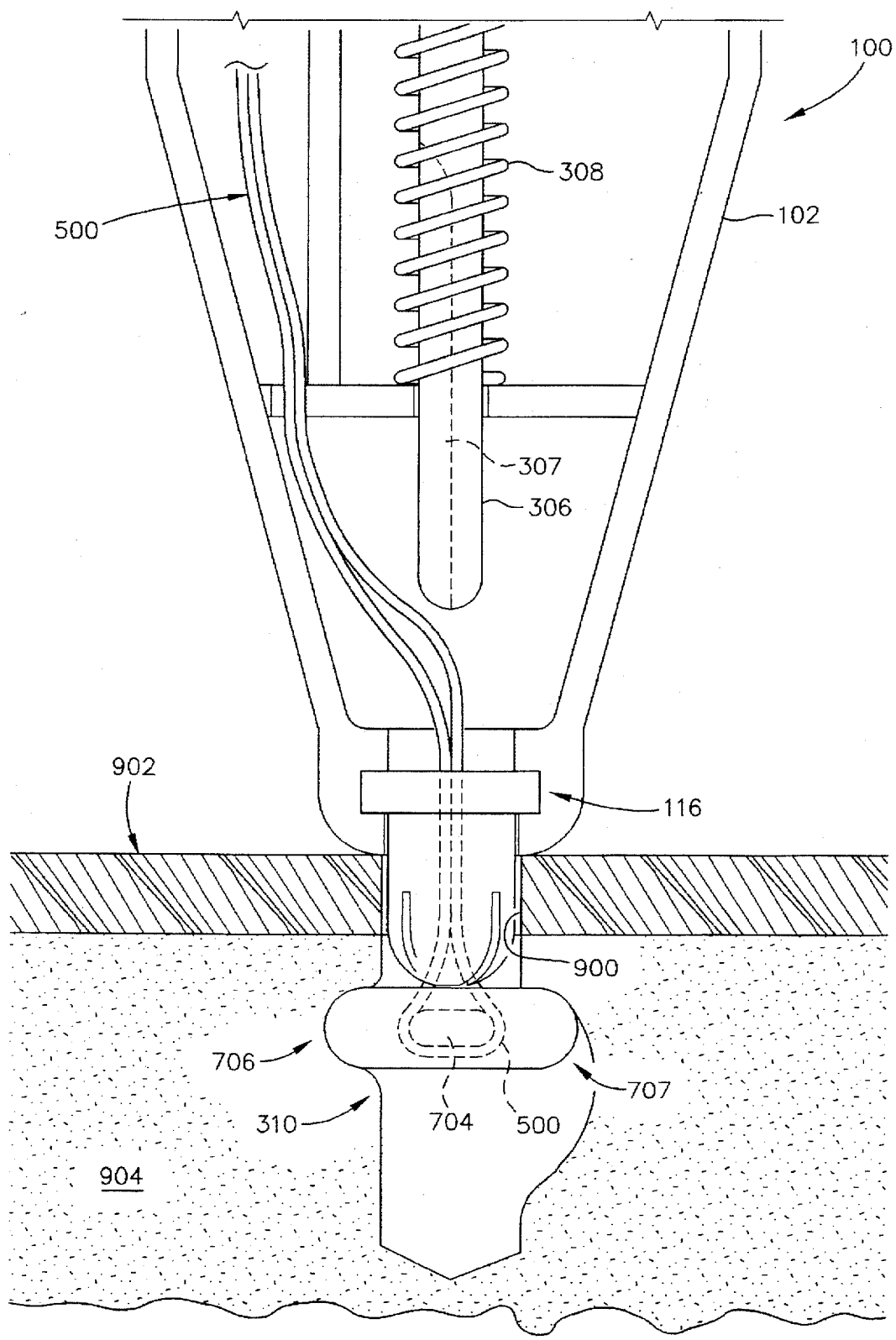
Figure 15:
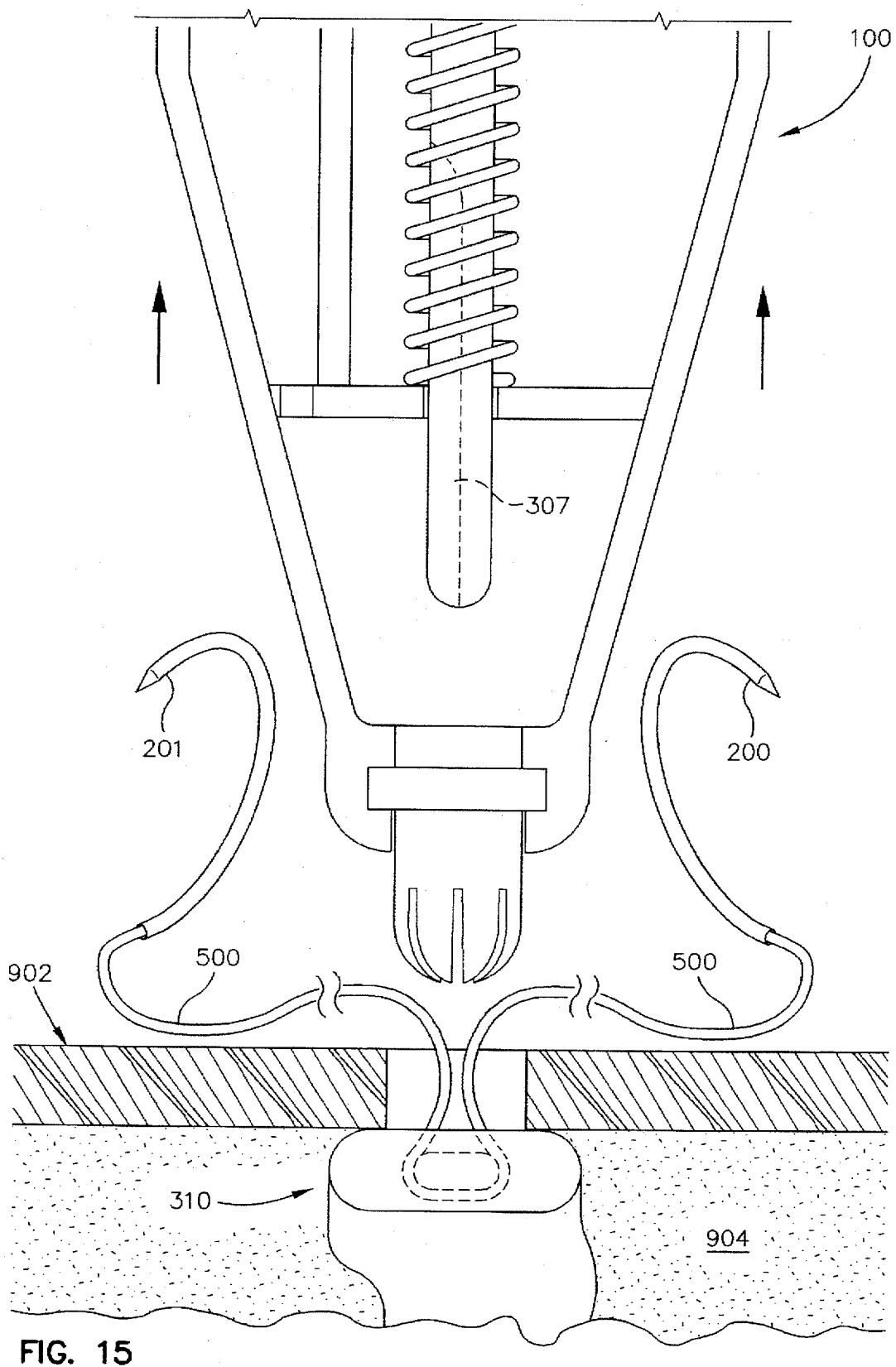

As shown in FIG. 14, further shortening of the tie 500 ultimately brings the anchor 310 into a lateral resting position, where the moment arm between the nose 116 and the bridge 704 is as small as possible. Namely, the bridge 704 is moved as close as possible to the nose 116. Although the anchor 310 resides in the cancellous layer 904, the anchor 310 abuts the cortical layer 902 and spans the hole 900, extending beyond edges of hole 900. Further tension on the tie 500 snugs the anchor 310 against the cortical layer 902.

Advantageously, since the anchor body defines either flat or gently rounded surfaces, tension on the anchor is evenly distributed along the inner surface of the patient's cortical bone. As a result, the anchor 310 is unlikely to damage, destroy, or be pulled completely through the cortical layer.

Removal & Disposal

Next, the tool 100 is separated from the tie 500. In particular, the tool 100 will be completely freed from the tie 500 after the tie 500 is separated from (1) the slot 118 defined in the housing 102, (2) the slot 307 defined in the extension 306, (3) and the slot 804 defined in the nose 116. After separating the tool 100 from the tie 500, the tool 100 may be disposed of, or sterilized and recycled.

Removing the tool 100 from the tie 500 leaves the anchor 310 firmly locked in place against the cortical layer 902. At this point, the physician can use one or both needles 200–201 to attach tissue such as muscle, tendon, or ligament to the bone, using the anchor 310 as a connecting point.

CONCLUSION

While there have been shown what are presently considered to be preferred embodiments of the invention, it will be apparent to those skilled in the art that various changes and modifications can be made herein without departing from the scope of the invention as defined by the appended claims. For example, in an alternative embodiment of the present invention, the tie is attached at one end to the anchor, but the other end may be bare. In accordance with such an alternative embodiment, no needles are present in the tool. If needles are required, they may be threaded after insertion of the anchor into the bone. Furthermore, the tie may be fixed to the anchor in any of a variety of ways. For example, the tie may be threaded through a bore which extends through the anchor. Alternatively, the tie may be retained within a recess by compressing the walls of the recess about the tie. Still further, while the bridge 704 is shown as being generally ellipsoid, the bridge may be formed in any shape which allows a tie to be threaded about anchor such that a generally upward force may be applied to the bridge by pulling upon the tie. Still further, the particular construction of the tool used to implant the anchor may vary from that shown. For example, in an alternative embodiment of the present invention, the tool may be constructed from more or less than two housing parts. Furthermore, in an alternative embodiment, no return spring is used to urge the plunger into a particular position. Also, the particular cutouts and other facilities shown for conveniently positioning the tie within the housing are not required. Accordingly, it should be understood that the invention is not to be limited by the specific illustrated embodiment, but only by the scope of the appended claims.

What is claimed is:

1. A method for anchoring a surgical tie to bone, the bone including a conical layer and a cancellous layer, the method comprising the steps of:

drilling an entry hole of a predetermined size in the bone, the entry hole extending through the cortical layer;

inserting into the entry hole a hollow tool having a distal end attached to a deflecting nose, the tool housing an elongated anchor that includes an anchor body and pair of opposing ends, the tool also housing a tie secured to the anchor;

advancing the anchor lengthwise through the tool, out the nose, through the conical layer, and into the cancellous layer;

tightening the tie sufficiently to pull an end of the anchor against the deflecting nose, and continuing to tighten the tie sufficiently to rotate the anchor against the deflecting nose until the anchor body is at angle to the entry hole;

withdrawing the tool from the entry hole; and locking the anchor in place by tightening the tie sufficiently to pull the anchor body firmly against the conical layer while spanning the entry hole such that opposing ends of the anchor extend beyond opposing edges of the bone surrounding the entry hole.

2. The method of claim 1, the advancing step being performed by extending a plunger through the tool against the anchor.

3. The method of claim 1, the steps of tightening the tie being performed by pulling at least one end of the tie.

4. The method of claim 1, the step of withdrawing the tool from the entry hole being performed after the step of locking the anchor in place.

5. The method of claim 1, the deflecting nose and the anchor ends having generally rounded shapes.

6. The method of claim 5, the deflecting nose comprising multiple rounded resilient fingers arranged about a passage though the nose.

7. The method of claim 1, the entry hole having a generally circular shape.

8. A method for anchoring a surgical tie to bone, the bone including a cortical layer and a cancellous layer, the method comprising the steps of:

drilling an entry hole of a predetermined size in the bone, the entry hole extending through the cortical layer;

inserting into the entry hole a hollow tool having a distal end attached to a deflecting nose having a passage defined therethrough, the tool housing an elongated anchor that includes an anchor body and pair of opposing ends, the tool also housing a surgical tie secured to the anchor;

advancing the anchor lengthwise through the tool, out the nose, through the cortical layer, and into the cancellous layer;

tightening the tie sufficiently to pull an end of the anchor against the deflecting nose;

continuing to tighten the tie sufficiently to rotate the anchor against the deflecting nose such that further tightening of the tie after withdrawal of the deflecting nose from the entry hole would snug the anchor body against the cortical layer;

withdrawing the tool from the entry hole; and further tightening the tie to pull the anchor body firmly against the cortical layer while spanning the entry hole such that the opposing ends of the anchor extend beyond opposing edges of the bone surrounding the entry hole.

9. An apparatus for anchoring a surgical tie to bone, comprising:

a hollow tool having a distal end attached to a deflecting nose, the nose having a passage defined therethrough;

an elongated anchor housed within the tool, the anchor including an anchor body and pair of opposing ends;

a tie housed within the tool and secured to the anchor; and a plunger slidably housed within the tool for movement through the tool to advance the anchor through the tool and out through the deflecting nose;

wherein the deflecting nose and anchor ends are curved such that, when an anchor end is urged against the nose, the nose rotates the anchor by deflecting the anchor end.

10. The apparatus of claim 9, the deflecting nose comprising multiple round resilient fingers arranged about the passage.

11. The apparatus of claim 9, the anchor ends having rounded shapes.

12. The apparatus of claim 9, the anchor including a pair of sides interconnected by a bridge.

13. The apparatus of claim 12, the bridge being centrally mounted with respect to the anchor sides.

14. The apparatus of claim 9, further comprising a pair of needles secured by the housing, wherein the surgical tie includes two ends each attached to a different one of the needles.

15. The apparatus of claim 14, the plunger including a biasing wedge positioned to arrange the needles for removal by an operator when the plunger moves past a predetermined position within the tool.

16. The apparatus of claim 9, the plunger and deflecting nose defining a continuous slot for passage of the surgical tie.

17. An anchor for attaching a surgical tie to bone, comprising:

an elongated body, comprising:
a first side having a substantially flat inner surface and a rounded outer surface, the first side being elongated and having rounded opposing ends; and
a second side having a substantially flat inner surface and a rounded outer surface, the second side being elongated and having rounded opposing ends; and
a bridge interconnecting the flat inner surfaces of the first and second sides, the first and second sides being positioned in parallel alignment to form two opposing sets of adjacent rounded ends.

18. An anchor for attaching a surgical tie to bone, comprising:

an elongated, generally capsule-shaped body, comprising:
a first side having a substantially flat inner surface and a rounded outer surface, the first side being elongated and having rounded opposing ends; and
a second side having a substantially flat inner surface and a rounded outer surface, the second side being elongated and having rounded opposing ends;
wherein the first and second sides are positioned in parallel alignment to form two sets of adjacent rounded ends; and
a bridge interconnecting the flat inner surfaces of the first and second sides.

19. A method for anchoring a surgical tie to bone, said bone including a cortical layer and a cancellous layer, said method comprising the steps of:

drilling an entry hole of a predetermined size in the bone, said entry hole extending through the cortical layer;

inserting into the entry hole a deflecting nose housing an elongated anchor that includes an anchor body and pair of opposing ends, said anchor body being secured to a surgical tie;

advancing the anchor lengthwise through the nose and into the cancellous layer;

tightening the tie sufficiently to pull an end of the anchor against the deflecting nose, and continuing to tighten the tie sufficiently to rotate the anchor against the deflecting nose until the anchor body is at angle to the entry hole;

locking the anchor in place by tightening the tie sufficiently to pull the anchor body firmly against the cortical layer while spanning the entry hole such that opposing ends of the anchor extend beyond opposing edges of the bone surrounding the entry hole.

* * * * *